(12) United States Patent
Liu et al.

(10) Patent No.: US 11,087,524 B2
(45) Date of Patent: Aug. 10, 2021

(54) METHOD FOR ESTABLISHING SMOOTH GEOMETRIC MODEL BASED ON DATA OF MEDICAL IMAGE

(71) Applicant: NEUBORON MEDTECH LTD., Jiangsu (CN)

(72) Inventors: Yuan-Hao Liu, Jiangsu (CN); Ming-Chen Hsiao, Jiangsu (CN)

(73) Assignee: NEUBORON MEDTECH LTD., Nanjing (CN)

( * ) Notice: Subject to any disclaimer, the term of this patent is extended or adjusted under 35 U.S.C. 154(b) by 0 days.

(21) Appl. No.: 16/459,952

(22) Filed: Jul. 2, 2019

(65) Prior Publication Data

US 2019/0325637 A1    Oct. 24, 2019

Related U.S. Application Data

(63) Continuation of application No. PCT/CN2017/092746, filed on Jul. 13, 2017.

(30) Foreign Application Priority Data

Jan. 11, 2017   (CN) .......................... 201710017475.5

(51) Int. Cl.
*G06T 15/08* (2011.01)
*G06T 5/00* (2006.01)
*G06T 17/00* (2006.01)

(52) U.S. Cl.
CPC .............. *G06T 15/08* (2013.01); *G06T 5/002* (2013.01); *G06T 17/00* (2013.01); *G06T 2210/41* (2013.01)

(58) Field of Classification Search
None
See application file for complete search history.

(56) References Cited

U.S. PATENT DOCUMENTS

| 8,139,709 B2 | 3/2012 | Noo |
| 2006/0110017 A1 | 5/2006 | Tsai et al. |

(Continued)

FOREIGN PATENT DOCUMENTS

| CN | 101082983 A | 12/2007 |
| CN | 101249019 A | 8/2008 |

(Continued)

OTHER PUBLICATIONS

Karasev, Peter, et al. "Interactive medical image segmentation using PDE control of active contours." IEEE transactions on medical imaging 32.11 (2013): 2127-2139 (Year: 2013).*

(Continued)

*Primary Examiner* — Sarah Le
(74) *Attorney, Agent, or Firm* — Locke Lord LLP; Tim Tingkang Xia, Esq.

(57) ABSTRACT

In one aspect, a method for establishing a smooth geometric model based on data of a medical image includes: inputting or reading the data of the medical image; establishing a three-dimensional medical image voxel model based on the data of the medical image; smoothing the three-dimensional medical image voxel model; and establishing a three-dimensional voxel phantom tissue model based on the smoothed three-dimensional medical image voxel model. In another aspect, a method for establishing a smooth geometric model based on data of a medical image includes: inputting or reading the data of the medical image; establishing a three-dimensional voxel phantom tissue model based on the data of the medical image; and smoothing the three-dimensional voxel phantom tissue model.

13 Claims, 5 Drawing Sheets

(56) References Cited

U.S. PATENT DOCUMENTS

| | | | |
|---|---|---|---|
| 2007/0282575 A1 | | 12/2007 | Gossage |
| 2009/0231334 A1 | * | 9/2009 | Chen ..................... G06T 17/205 |
| | | | 345/420 |
| 2011/0150312 A1 | | 6/2011 | Takanami et al. |
| 2013/0135305 A1 | * | 5/2013 | Bystrov ..................... G06T 7/11 |
| | | | 345/420 |
| 2015/0213646 A1 | | 7/2015 | Ma et al. |
| 2016/0314584 A1 | | 10/2016 | Hennix et al. |
| 2017/0301085 A1 | * | 10/2017 | Riklin Raviv .......... G06F 19/00 |
| 2018/0061077 A1 | * | 3/2018 | Grimm .................. G16H 50/20 |

FOREIGN PATENT DOCUMENTS

| | | | |
|---|---|---|---|
| CN | 101751697 A | | 6/2010 |
| CN | 102580230 A | | 7/2012 |
| CN | 104267425 A | | 1/2015 |
| CN | 103065358 B | | 3/2015 |
| CN | 106163403 A | | 11/2016 |
| EP | 1658878 A1 | * | 5/2006 ........... A61N 5/1031 |
| JP | 2012088771 A | | 5/2012 |
| TW | 200616586 A | | 6/2006 |
| WO | 2006138513 A1 | | 12/2006 |
| WO | 2010005119 A1 | | 1/2010 |

OTHER PUBLICATIONS

Reynaert, Nick, et al. "Monte Carlo treatment planning for photon and electron beams." Radiation Physics and Chemistry 76.4 (2007): 643-686. (Year: 2007).*

Daquino, G. G. Treatment Planning Systems for BNCT: Requirements and Peculiarities. No. CERN-OPEN-2003-052. 2003 (Year: 2003).*

Lee, Choonsik, et al. "NURBS-based 3-D anthropomorphic computational phantoms for radiation dosimetry applications." Radiation protection dosimetry 127.1-4 (2007): 227-232 (Year: 2007).*

Mathworks, "Partial Differential Equation Toolbox User's Guide", posted Aug. 2014, http://www.math.ntu.edu.tw/~shyue/myclass/pde00/misc/pde.pdf (Year: 2014).*

Ali Alghamdi, "Voxel-based anthropomorphic phantoms with Monte Carlo simulations in neutron dosimetry", 2006 (Year: 2006).*

Cronholm, Rickard. "Monte Carlo Treatment Planning for Advanced Radiotherapy." (2012) (Year: 2012).*

Sarah F. F. Gibson, Constrained Elastic Surface Nets: Generating Smooth Surfaces from Binary Segmented Data, XP-000965032, 1998.

International Search Report of PCT/CN2017/092746, dated Oct. 24, 2017.

* cited by examiner

METHOD FOR ESTABLISHING SMOOTH GEOMETRIC MODEL BASED ON DATA OF MEDICAL IMAGE

CROSS-REFERENCE TO RELATED PATENT APPLICATION

This application is a continuation application of International Application No. PCT/CN2017/092746, filed on Jul. 13, 2017, which claims priority to Chinese Patent Application No. 201710017475.5, filed on Jan. 11, 2017, the disclosures of which are hereby incorporated by reference.

FIELD

The present disclosure relates to a method for establishing a geometric model, and in particular to a method for establishing a smooth geometric model based on data of a medical image.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

BNCT takes advantage that the boron ($^{10}$B)-containing pharmaceuticals have high neutron capture cross section and produces $^{4}$He and $^{7}$Li heavy charged particles through $^{10}$B(n,α)$^{7}$Li neutron capture and nuclear fission reaction. The total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

Three-dimensional model is widely used in scientific experiment analysis, scientific experiment simulation field. For example, in the field of nuclear radiation and protection, in order to simulate the dose absorbed by the living organisms under certain radiation conditions, it is often necessary to process the medical image by using computer technology to establish an accurate lattice model required by MCNP and combine with MCNP (Monte Carlo Program) for simulation.

At present, the Monte Carlo method is a tool that could accurately simulate the collision trajectory and energy distribution of the nuclear particle in the three-dimensional space of the irradiated target. The combination of the Monte Carlo method with a complex three-dimensional human anatomy model represents a leap forward of simulation in computer technology. In diagnostic radiographic examination, accurate human organ dose assessment is very beneficial for radiation therapy. At present around the world, a variety of human models have been successfully established and combined with Monte Carlo simulation program to evaluate the accuracy of the human body's absorbed dose in the radiation environment. It is a prerequisite for Monte Carlo simulation to successfully transform the three-dimensional anatomical model of human body into geometric description required by Monte Carlo program. It is also the hot and difficult point of Monte Carlo simulation in the world at present.

Figure 4:
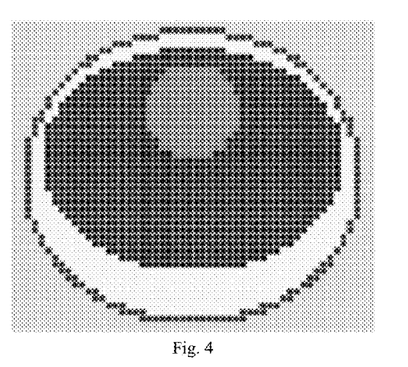
FIG. 4 is a schematic diagram of a voxel model that has not been subjected to smoothing processing.

Medical image such as Magnetic Resonance Imaging (MRI) or Computed Tomography (CT) could provide detailed tissue geometry information for human body features, providing data basis for physical modeling of human internal structures. In the field of neutron capture therapy, it is a very important topic how to establish a geometric model required for MCNP based on medical image data, that is, a lattice model or voxel phantom tissue model required for MCNP software input file. At present, the common MCNP geometric model is based on a small cube (voxel) as the basic element, which are constructed according to the information contained in the medical image. Therefore, the contour of the voxel model is presented as steps, as shown in FIG. 4, and there is a certain degree of error with the contour of the surface of human organs and tissues, which in turn affects the reliability of the dose calculation result.

Therefore, it is necessary to propose a method for establishing a smooth geometric model based on data of a medical image to improve the reliability of dose calculation and the quality of treatment.

SUMMARY

An aspect of the present disclosure provides a method for establishing a smooth geometric model based on data of a medical image, including: inputting or reading the data of the medical image; establishing a three-dimensional medical image voxel model based on the data of the medical image; smoothing the three-dimensional medical image voxel model; and establishing a three-dimensional voxel phantom tissue model based on the smoothed three-dimensional medical image voxel model.

Another aspect of the present disclosure provides a method for establishing a smooth geometric model based on data of a medical image, including: inputting or reading the data of the medical image; establishing a three-dimensional voxel phantom tissue model based on the data of the medical image; and smoothing the three-dimensional voxel phantom tissue model.

The method for establishing a smooth geometric model smoothes the three-dimensional medical image voxel model or the three-dimensional voxel phantom tissue model to make it closer to the real situation of the human organ, thereby improving the reliability of the dose calculation.

More particularly, the three-dimensional medical image voxel model or the three-dimensional voxel phantom tissue model is smoothed by: defining or reading an ROI boundary; and smoothing the ROI boundary.

The so-called ROI refers to Region Of Interest (hereinafter collectively referred to as ROI). The ROI boundary referred to in the present disclosure is not limited to the outer contour of a key organ, but also includes a tissue boundary in which the density is significantly changed, an outer contour of the irradiation site, or a tumor cell outer contour.

More particularly, the ROI boundary is smoothed by: describing the ROI boundary as a partial differential equation; and solving the partial differential equation to obtain a solution and correcting the ROI boundary according to the solution.

More particularly, the ROI boundary is smoothed by a finite element analysis software.

More particularly, the ROI boundary is pre-defined and/or newly added in the data of the medical image, and the newly added ROI boundary is obtained by automatic judgment and/or manual selection, wherein the ROI boundary includes multiple sub-geometric domains being described by partial differential equations.

More particularly, the voxel phantom tissue model carries tissue type and tissue density information. The voxel phantom tissue model is established based on the conversion relationship between the data of the medical image and tissue types and density values. The quantity of tissue clusters may be determined according to actual requirements, so that the tissue type, the element composition and the tissue density are provided more accurately, and an established geometric model is better matched to the real situation reflected by the medical image data.

Further, the three-dimensional voxel phantom tissue model is established by: defining a type of a tissue according to a conversion relationship between the data of the medical image and tissue types; determining a quantity of tissue clusters of the tissue; defining a density of the tissue by a conversion relationship between the data of the medical image and density values; and establishing a 3D encoding matrix with information about the tissue and the density.

Alternatively, the three-dimensional voxel phantom tissue model is established by: determining whether each of a plurality of medical image voxels in the data of the medical image is within the ROI boundary; when one of the medical image voxels is determined to be within the ROI boundary, performing manually defining a type and a density of a tissue by assigning a particular tissue and density to the one of the medical image voxels within the ROI boundary, or performing: automatically defining a type of a ROI tissue according to a conversion relationship between the data of the medical image and tissue types, determining a quantity of tissue clusters of the ROI tissue, and automatically defining a density of the ROI tissue by a conversion relationship between the data of the medical image and density values; when one of the medical image voxels is determined not to be within the ROI boundary, performing: automatically defining the type of the tissue according to the conversion relationship between the data of the medical image and the tissue types, determining the quantity of the tissue clusters of the tissue, and automatically defining the density of the tissue by the conversion relationship between the data of the medical image and the density values; and establishing a 3D encoding matrix with information about the tissue and the density. The user could manually define the tissue type, elements composition and density of ROI.

More particularly, the voxel phantom tissue model also carries tissue boron concentration information, the three-dimensional voxel phantom tissue model is established by further assigning a Boron-10 concentration and establishing the 3D encoding matrix with information of the Boron-10 concentration. The geometric model labeled with boron concentration information clearly shows that the concentration of the boron-containing drug in each tissue and then when performing neutron capture therapy simulation, it is more realistic to reflect the actual situation.

More particularly, the quantity of the tissue clusters is a quantity of the tissue clusters manually defined by a user, plus a quantity of four tissue clusters or fourteen tissue clusters already existing in the database. If there is no established corresponding quantity of the tissue clusters in the existing database, a new quantity of the tissue clusters can be defined by the user. This avoids the situation where only approximate choices can be made if the corresponding quantity of the tissue clusters cannot be exactly matched in an existing database, thereby effectively improving the accuracy of the modeling.

More particularly, the three-dimensional voxel phantom tissue model is established by further establishing a 3D tissue encoding matrix and establishing a 3D density encoding matrix. According to the slice of the data of the medical image, the corresponding tissue encoding and density encoding are established for each slice through the corresponding transformation relations so as to establish the 3D tissue encoding matrix and the 3D density encoding matrix.

More particularly, the method may be applied to neutron capture therapy, and the smooth geometric model includes a lattice card, a cell card, a surface card and a material card required by the input file of MCNP software. Through the medical image data, the lattice card, the cell card, the surface card and the material card required by the input file of MCNP software may be finally obtained, thereby providing a theoretical basis for the simulation calculation and obtaining accurate simulation calculation results.

Medical image data may be Magnetic Resonance Imaging (MRI), Computed Tomography (CT), Positron Emission Tomography (PET), PET-CT or X-ray imaging. The following embodiments will be described based on the data of Computed Tomography, the file format of which is usually DICOM. However, it is well known to those skilled in the art that other medical image data may also be used, as long as the medical image data may be converted into a three-dimensional MCNP phantom tissue model, it may be applied to the method for establishing a smooth geometric model based on medical image data disclosed by the present disclosure.

The method in the embodiments of the disclosure could greatly improve the stepped contour of the voxel phantom and improve the reliability of the dose calculation to improve the quality of treatment.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure.

Wherever possible, the same reference numbers are used throughout the drawings to refer to the same or like elements of an embodiment.

DETAILED DESCRIPTION OF THE DISCLOSURE

The embodiments of the present disclosure are further described in detail below with reference to the accompanying drawings, so that those skilled in the art can implement the technical solutions according to the description.

A method for establishing a smooth geometric model based on medical image data for neutron capture therapy may be taken as embodiments of the present disclosure. The following will briefly introduce neutron capture therapy, especially boron neutron capture therapy.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components include, in general, an accelerator for accelerating charged particles (such as protons and deuterons), a target, a heat removal system and a beam shaping assembly. The accelerated charged particles interact with the metal target to produce the neutrons. Suitable nuclear reactions are always determined according to such characteristics as desired neutron yield and energy, available accelerated charged particle energy and current and materialization of the metal target, among which the most discussed two are $^7Li$ (p, n)$^7Be$ and $^9Be$ (p, n)$^9B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be provided clinically without many moderations. However, Li (lithium) and Be (beryllium) and protons of threshold energy exhibit not high action cross section. In order to produce sufficient neutron fluxes, high-energy protons are usually selected to trigger the nuclear reactions.

Figure 1:
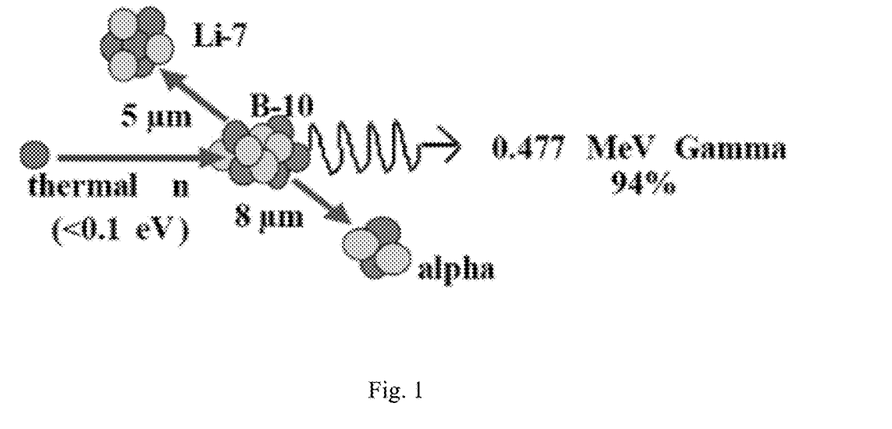
FIG. 1 is a schematic view of boron neutron capture reaction.
Figure 2:
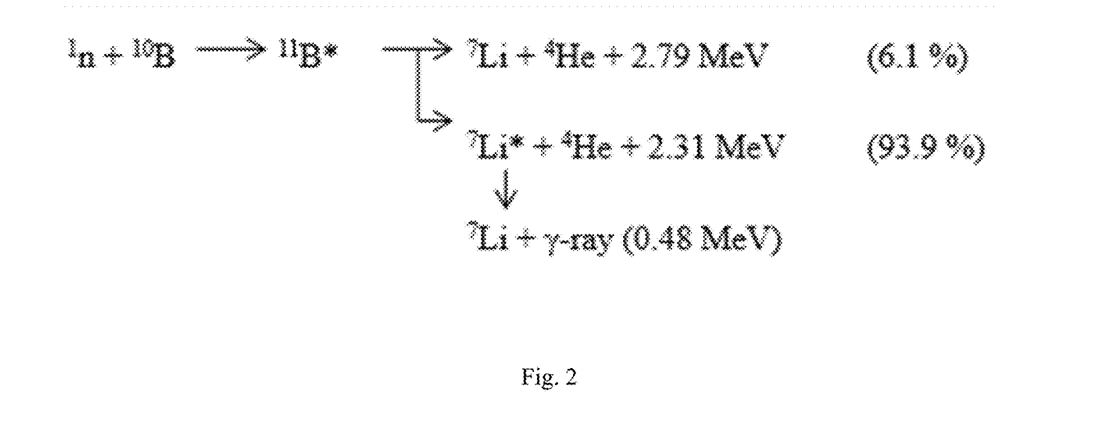
FIG. 2 is a nuclear reaction formula of $^{10}B(n,\alpha)^7Li$ neutron capture.

BNCT takes advantage that the boron ($^{10}B$)-containing pharmaceuticals have high neutron capture cross section and produces $^4He$ and $^7Li$ heavy charged particles through $^{10}B(n,\alpha)^7Li$ neutron capture and nuclear fission reaction. As illustrated in FIGS. 1 and 2, a schematic drawing of BNCT and a nuclear reaction formula of $^{10}B$ (n,α)$^7Li$ neutron capture are shown, the two charged particles, with average energy at about 2.33 MeV, are of linear energy transfer (LET) and short-range characteristics. LET and range of the alpha particle are 150 keV/μm and 8 μm respectively while those of the heavy charged particle $^7Li$ are 175 keV/μm and 5 μm respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

It is an object of the embodiments of the present disclosure to convert medical image data into a three-dimensional MCNP voxel phantom tissue model which is more like the contour of the organ and tissue of a living organisms, especially a human body, for performing a tissue dose simulation calculation of boron neutron capture therapy. Medical image data may be Magnetic Resonance Imaging (MRI), Computed Tomography (CT), Positron Emission Tomography (PET), PET-CT or X-ray imaging. The present embodiments will be described based on the data of Computed Tomography, the file format of which is usually DICOM. However, it is well known to those skilled in the art that other medical image data may also be used as long as the medical image data may be converted into a three-dimensional MCNP phantom tissue model, it may be applied to the method for establishing a smooth geometric model based on medical image data disclosed by the present disclosure.

Figure 3:
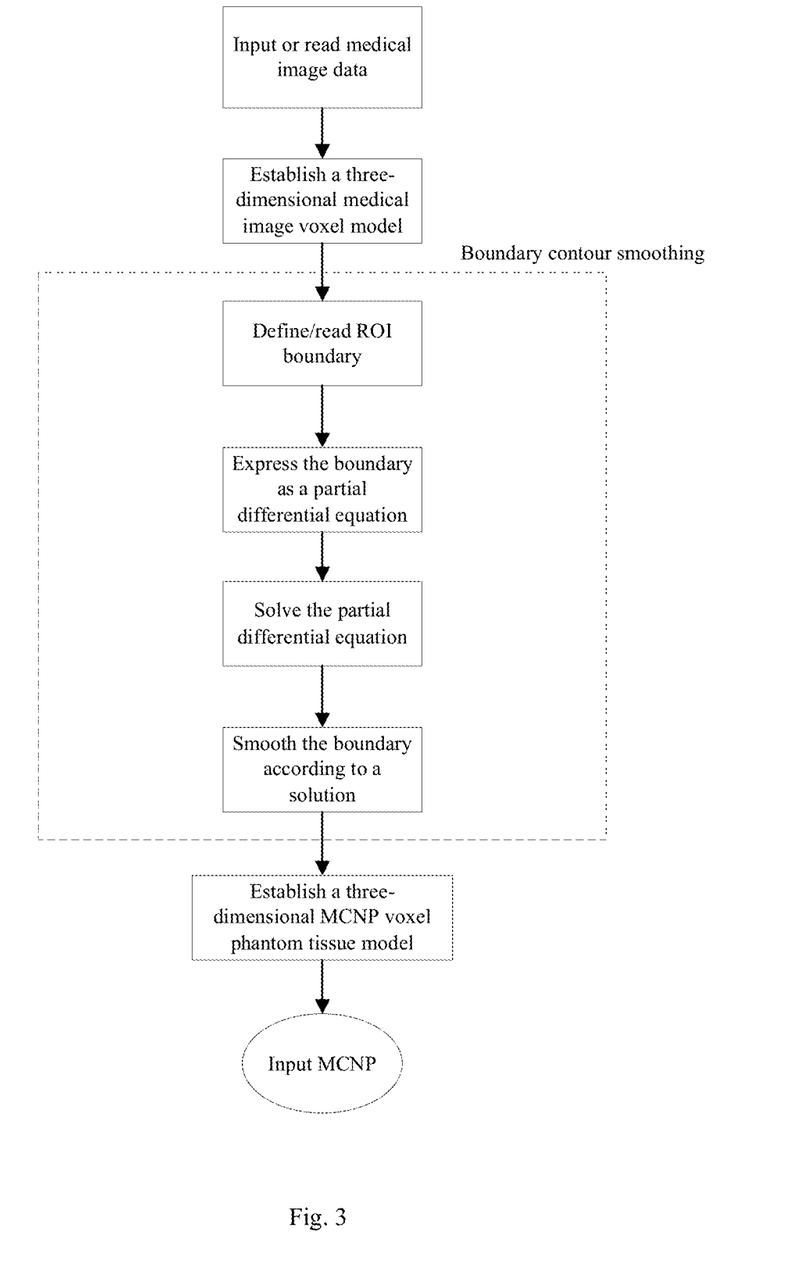
FIG. 3 is a logic block diagram of a method for establishing a smooth geometric model based on medical image data according to an embodiment of the present disclosure.

Referring to FIG. 3, the method for establishing a smooth geometric model based on data of a medical image disclosed in the embodiment of the present disclosure mainly includes the following process:

1. Inputting or reading computerized tomographic image data (in DICOM format), the CT image data would be presented on the corresponding interface;

2. Establishing a three-dimensional medical image voxel model based on the data of the medical image;

3. Automatically reading the pre-defined ROI boundary in the DICOM file, or adding another ROI boundary;

4. Smoothing the boundary;

5. According to the conversion relationship between CT image data and tissue type (element composition) and density, defining the tissue type (element composition) and tissue density of each voxel unit, and establishing a three-dimensional MCNP voxel phantom tissue model.

In certain embodiments, the ROI boundary could be the outer contour of a key organ such as the eye, liver, and the like; the boundary of different types (significantly changed density) of tissues such as bones and soft tissues; the outer contour of the irradiated portion, such as the head; and the outer contour of the tumor cell.

Step 5 above may be at any position after step 1. When it is between steps 1 and 3, step 2 may be omitted, that is, the three-dimensional MCNP voxel phantom tissue model may be directly established according to CT image data, and then the boundary is selected and processed, at this time, it is the ROI boundary in the three-dimensional MCNP voxel phantom tissue model that is smoothed. The three-dimensional medical image voxel model obtained from CT image data or the three-dimensional MCNP voxel phantom tissue model thus established is based on a small cube as the basic element, therefore, the contour of the voxel model is presented as steps, as shown in FIG. 4, and there is a certain degree of error with the contour of the curved surface of living organs and tissues, which in turn affects the reliability of the dose calculation result. The newly added ROI boundary in step 3 could be obtained by automatic determined and/or manual selection. The manner of automatically determining the ROI boundary may be various, such as discriminating the position of each voxel unit, calculating the difference or difference ratio between the voxel values of the voxel unit and all adjacent voxel units, considering the voxel unit to be at the boundary when the difference or difference ratio with one of the adjacent voxel elements is greater than a certain range, and selecting all voxel units at the boundary. Certainly, different types of tissues have different voxel value ranges. Therefore, different boundaries have different ranges of comparison values. According to different ranges of comparison values, the voxel units at the boundary are distinguished, and according to the obtained result, the required ROI boundary can be manually selected again. Such selection is based on the results of automated calculation, which is more intelligent and accurate. The ROI boundary could also be automatically calculated based on the results. In addition, according to the CT image, data and 3D medical image voxel model, 3D MCNP voxel phantom tissue model, combined with their own experience, doctors or operators could directly select the ROI boundary that needs to be smoothed on the model or correct the above-mentioned automatically obtained ROI boundary.

In step 4, the boundary smoothing process is performed. Specifically, the ROI boundary obtained in step 3, i.e., the stepped outer contour, is described by a partial differential equation. It should be understood that the description of the boundary is not limited to the partial differential equation, as long as it is a mathematical method capable of describing the boundary. The ROI boundary may include multiple closed or unclosed components, each of which may also need to be divided into multiple sub-geometric domains that could be described by partial differential equations. Then, each partial differential equation is solved, for example, a finite element method is provided to find the approximate solution of the partial differential equation, and each sub-geometric domain is corrected to a smooth boundary component according to the solving result, and then integrated into the entire smooth ROI boundary, that is, the stepped outer contour is corrected to an outer contour with smooth curved surface. Certainly, commercially available software such as the finite element analysis software Abaqus\CAE may also be provided for the above processing.

Figure 5:
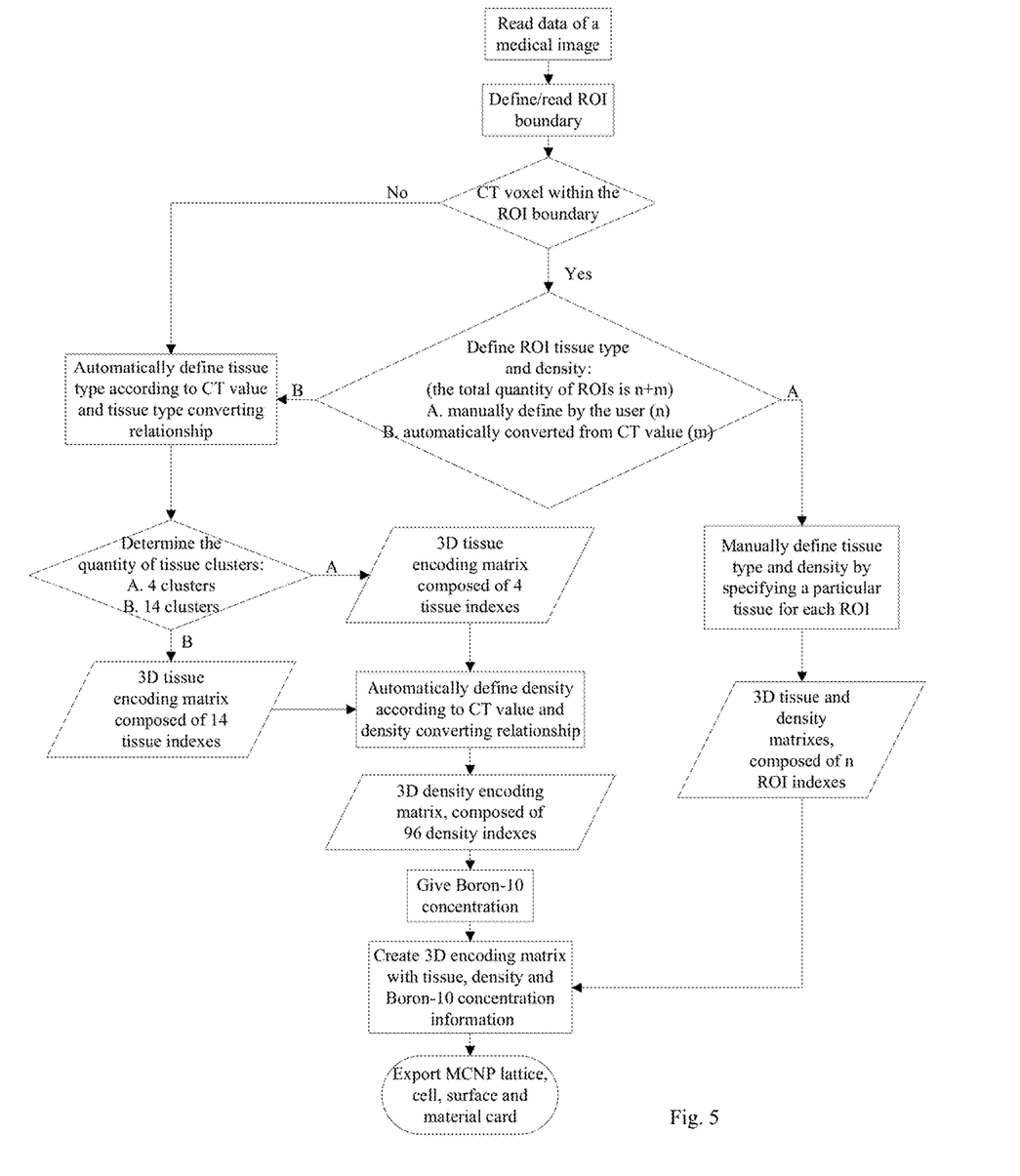
FIG. 5 is a logic block diagram of a method for establishing a three-dimensional voxel phantom tissue model according to an embodiment of the present disclosure.

Referring to FIG. 5, the method for establishing a three-dimensional MCNP voxel phantom tissue model in step 5 specifically includes two embodiments.

One aspect of the present disclosure is to provide a geometric model (three-dimensional MCNP voxel phantom tissue model) establishment method based on the data of the medical image, the method including: defining a type of a tissue by a conversion relationship between the data of the medical image and the tissue types; determining a quantity of tissue clusters; defining a density of the tissue by a conversion relationship between the data of the medical image and density values; establishing a 3D encoding matrix with information about the tissue and the density; and generating a geometric model.

According to a conversion relationship between the data of the medical image and tissue types, the quantity of tissue clusters may be determined according to actual requirements, so that the tissue type, the element composition and the density may be provided more accurately, and an established geometric model may be better matched to the real situation reflected by the data of the medical image.

The geometric model establishment method further includes assigning a Boron-10 concentration and establishing a 3D encoding matrix with information of the Boron-10 concentration. The geometric model labeled with Boron-10 concentration information clearly shows that the concentration of the boron-containing drug in each tissue and then when performing neutron capture therapy simulation, it may be more realistic to reflect the actual situation.

The quantity of the tissue clusters may be a quantity of the tissue clusters manually defined by the user plus a quantity of the four tissue clusters or fourteen tissue clusters already existing in the database. If there is no established corresponding quantity of the tissue clusters in the existing database, a new quantity of the tissue clusters may be defined by the user. This avoids the situation where only approximate choices may be made if the corresponding quantity of the tissue clusters could not be exactly matched in an existing database, thereby effectively improving the accuracy of the modeling.

The geometric model establishment method further includes establishing a 3D tissue encoding matrix and establishing a 3D density encoding matrix. According to the slice of the medical image data, the corresponding tissue encoding and density encoding may be established for each slice through the corresponding transformation relations so as to establish the 3D tissue encoding matrix and the 3D density encoding matrix.

The geometric model includes a lattice card, a cell card, a surface card and a material card required by the input file of MCNP software. Through the medical image data, the lattice cards, cell card, surface card and material card required by the input file of MCNP software are finally obtained, which provide a theoretical basis for simulation calculation and obtain accurate simulation results.

Another aspect of the present disclosure is to provide a geometric model establishment method including: defining or reading an ROI boundary; determining whether each of a plurality of medical image voxels is within the ROI boundary; when one of the medical image voxels is determined to be within the ROI boundary, performing manually defining a type and a density of a ROI tissue by assigning a particular tissue and density to the one of the medical image voxels within the ROI boundary or performing automatically defining a type and a density of the ROI tissue by a conversion relationship between the data of the medical image and the tissue types/density values, when one of the medical image voxels is determined not to be within the ROI boundary, performing automatically defining the type of the tissue by the conversion relationship between the data of the medical image and the tissue types, and defining the density of the tissue by the conversion relationship between the data of the medical image and the density values; establishing 3D encoding matrix with information about the tissue and the density; and generating a geometric model.

The user may manually define the tissue type, elemental composition and density of ROI. If the medical image voxel is not within the ROI boundary, the definition of the tissue type is performed according to the conversion relationship between the data of the medical image and the tissue types/density values, and the quantity of tissue clusters may be determined according to the actual needs so as to provide the tissue type, the element composition and the density more accurately, and the established geometric model more closely matches the real situation reflected by the medical image data.

The geometric model establishment method further includes assigning a Boron-10 concentration and establishing the 3D encoding matrix with information of the Boron-10 concentration. The geometric model labeled with Boron-10 concentration information clearly shows that the concentration of the boron-containing drug in each tissue and then when performing neutron capture therapy simulation, it may be more realistic to reflect the actual situation.

The quantity of the tissue clusters is a quantity of the tissue clusters manually defined by the user plus a quantity of the four tissue clusters or fourteen tissue clusters already existing in the database. If it covers a wide range of CT values within a single ROI boundary (e.g. mucosal chamber), the CT value may be automatically matched with the tissue type and density, so as to avoid the error of dose calculation because of assigning unique tissue type (elemental composition) and density. If there is no established corresponding number of the tissue clusters in the existing database, a new number of the tissue clusters may be defined by the user. This avoids the situation where only approximate choices may be made if the corresponding number of the tissue clusters cannot be exactly matched in an existing database, thereby effectively improving the accuracy of the modeling.

The geometric model establishment method further includes establishing a 3D tissue encoding matrix and establishing a 3D density encoding matrix. According to the slice of the medical image data, the corresponding tissue encoding and density encoding may be established for each slice through the corresponding transformation relations so as to establish the 3D tissue encoding matrix and the 3D density encoding matrix.

The geometric model includes a lattice card, a cell card, a surface card and a material card required by the input file of MCNP software. Through the medical image data, the lattice cards, cell card, surface card and material card required by the input file of MCNP software are finally obtained, which provide a theoretical basis for simulation calculation and obtain accurate simulation results.

Figure 6:
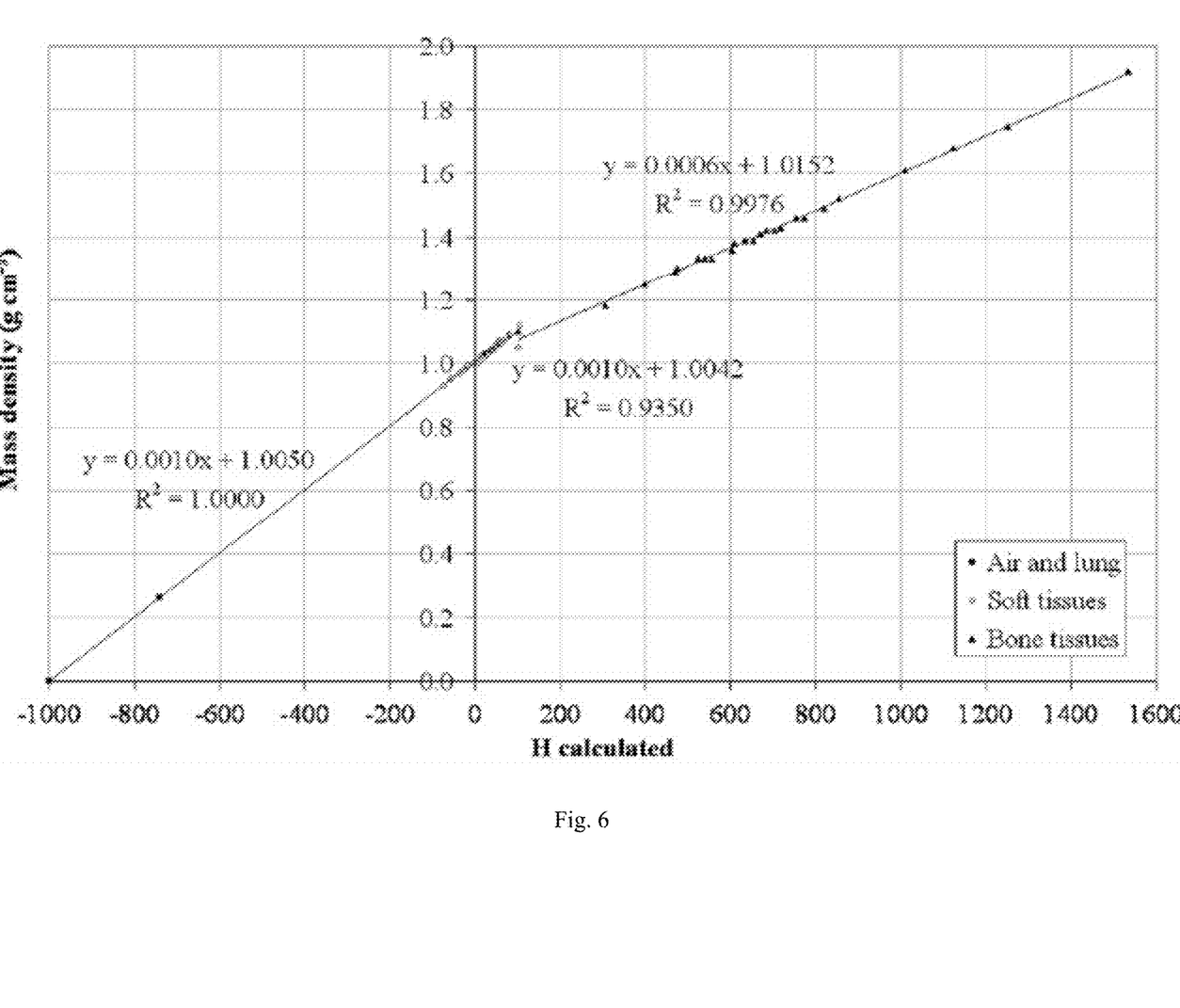
FIG. 6 is a chart showing regression curve formula and correlation coefficient of CT value (HU) and tissue density.

Referring to FIG. 6, the CT value-tissue type and CT value-tissue density conversion charts in the existing database in the method for establishing a geometric model disclosed in the present disclosure will be described below.

The CT value, also known as the Hounsfield Unit (HU or H), is the ratio of the linear attenuation coefficient of each tissue to that of water and is the unit representing light attenuation coefficient, which is defined as Formula 1:

$$HU = 1000\left(\frac{\mu\, eff}{\mu_{water}} - 1\right) \quad \text{Formula 1}$$

Reference was made to the literature published by Vanderstraeten et al. in 2007 (Barbara Vanderstraeten et al, "Conversion of CT numbers into tissue parameters for Monte Carlo dose calculations: a multi-center study", Phys. Med. Biol. 52 (2007) 539-562.), depending on the CT values, they can be converted into one type of air, one type of lung, two types of soft tissues (adipose and muscle) and ten types of bones, in other words, different CT values correspond to a total of 14 tissues consisted of different elements, as shown in Table 1 below.

TABLE 1

CT values correspond to 14 tissues composed of different elements (% by weight of elements)

| tissue | HU | H | C | N | O | Na | Mg | P | S | Cl | Ar | K | Ca |
|---|---|---|---|---|---|---|---|---|---|---|---|---|---|
| air | <−900 | | | 75.5 | 23.2 | | | | | | 1.3 | | |
| lung | −900~−100 | 10.3 | 10.5 | 3.1 | 74.9 | 0.2 | | 0.2 | 0.3 | 0.3 | | 0.2 | |
| adipose | −100~20 | 11.2 | 53.3 | 1.1 | 34.1 | 0.1 | | | 0.1 | 0.1 | | | |
| muscle | 20~100 | 10.1 | 15.6 | 4.0 | 69.3 | 0.3 | | 0.1 | 0.3 | 0.2 | | 0.1 | |
| bone | 100~250 | 9.5 | 45.3 | 2.5 | 35.5 | 0.1 | | 2.1 | 0.2 | 0.1 | | 0.1 | 4.6 |
| bone | 250~400 | 8.4 | 40.1 | 2.8 | 36.9 | 0.1 | 0.1 | 3.6 | 0.2 | 0.1 | | 0.1 | 7.7 |
| bone | 400~550 | 7.5 | 35.5 | 3.0 | 38.1 | 0.1 | 0.1 | 4.8 | 0.2 | 0.1 | | 0.1 | 10.5 |
| bone | 550~700 | 6.7 | 31.6 | 3.3 | 39.2 | 0.1 | 0.1 | 5.9 | 0.2 | 0.1 | | | 12.8 |
| bone | 700~850 | 6.0 | 28.1 | 3.5 | 40.1 | 0.1 | 0.1 | 6.8 | 0.2 | | | | 14.9 |
| bone | 850~1000 | 5.3 | 25.0 | 3.7 | 41.0 | 0.1 | 0.1 | 7.7 | 0.3 | | | | 16.8 |
| bone | 1000~1150 | 4.8 | 22.3 | 3.8 | 41.7 | 0.1 | 0.2 | 8.4 | 0.3 | | | | 18.4 |
| bone | 1150~1300 | 4.3 | 19.8 | 4.0 | 42.3 | 0.1 | 0.2 | 9.1 | 0.3 | | | | 19.9 |
| bone | 1300~1450 | 3.8 | 17.6 | 4.1 | 42.9 | 0.1 | 0.2 | 9.7 | 0.3 | | | | 21.2 |
| bone | >1450 | 3.4 | 15.6 | 4.2 | 43.5 | 0.1 | 0.2 | 10.3 | 0.3 | | | | 22.4 |

Reference was made to Report No. ICRU-46 (International Commission on Radiation Units and Measurements, Photon, electron, proton and neutron interaction data for body tissues, ICRU-46, Tech. Rep., 1992.), and four major human brain tissues were taken, including air, adult brain, adult skin and cranium, with the corresponding density and elemental composition shown in Table 2.

TABLE 2

CT values corresponding to four tissues composed of different elements (% by weight of elements)

| tissue | ρ (g/cm³) | H | C | N | O | Na | Mg | P | S | Cl | Ar | K | Ca |
|---|---|---|---|---|---|---|---|---|---|---|---|---|---|
| air | 0.001293 | | | 75.5 | 23.2 | | | | | | 1.3 | | |
| adult brain | 1.04 | 10.7 | 14.5 | 2.2 | 71.2 | 0.2 | | 0.4 | 0.2 | 0.3 | | 0.3 | |
| adult skin | 1.09 | 10.0 | 20.4 | 4.2 | 64.5 | 0.2 | | 0.1 | 0.2 | 0.3 | | 0.1 | |
| cranium | 1.61 | 5.6 | 21.2 | 4.0 | 43.5 | 0.1 | 0.2 | 8.1 | 0.3 | | | | 17.6 |

The same reference was made to the literature of Vanderstraeten et al., which unified the true experimental values from hospitals, and sorted out the relationship formula of CT value corresponding to tissue density, as shown in FIG. 6; the geometric model establishment method based on medical image data disclosed in the present disclosure used the three sets of regression formulas in FIG. 6 to classify CT values (−1000 to 2000) into 96 density clusters, as shown in Table 3.

TABLE 3

Conversion of CT value and mass density HUL and HUU being the lower and upper limits of CT value, respectively

| $HU_L$ | $HU_U$ | ρ (g/cm³) |
|---|---|---|
|  | −990 | 0.0050 |
| −990 | −980 | 0.0200 |
| −980 | −970 | 0.0300 |
| −970 | −960 | 0.0400 |
| −960 | −950 | 0.0500 |
| −950 | −925 | 0.0675 |
| −925 | −900 | 0.0925 |
| −900 | −875 | 0.1175 |
| −875 | −850 | 0.1425 |
| −850 | −825 | 0.1675 |
| −825 | −800 | 0.1925 |
| −800 | −775 | 0.2175 |
| −775 | −750 | 0.2425 |
| −750 | −725 | 0.2675 |
| −725 | −700 | 0.2925 |
| −700 | −650 | 0.3300 |
| −650 | −600 | 0.3800 |
| −600 | −550 | 0.4300 |
| −550 | −500 | 0.4800 |
| −500 | −450 | 0.5300 |
| −450 | −400 | 0.5800 |
| −400 | −350 | 0.6300 |
| −350 | −300 | 0.6800 |
| −300 | −250 | 0.7300 |
| −250 | −200 | 0.7800 |
| −200 | −175 | 0.8175 |
| −175 | −150 | 0.8425 |
| −150 | −125 | 0.8675 |
| −125 | −100 | 0.8925 |
| −100 | −80 | 0.9142 |
| −80 | −60 | 0.9342 |
| −60 | −40 | 0.9542 |
| −40 | −20 | 0.9742 |
| −20 | 0 | 0.9942 |
| 0 | 20 | 1.0142 |
| 20 | 40 | 1.0342 |
| 40 | 60 | 1.0542 |
| 60 | 80 | 1.0742 |
| 80 | 100 | 1.0942 |
| 100 | 125 | 1.0827 |
| 125 | 150 | 1.0977 |
| 150 | 175 | 1.1127 |
| 175 | 200 | 1.1277 |
| 200 | 225 | 1.1427 |
| 225 | 250 | 1.1577 |
| 250 | 275 | 1.1727 |
| 275 | 300 | 1.1877 |
| 300 | 325 | 1.2027 |
| 325 | 350 | 1.2177 |
| 350 | 375 | 1.2327 |
| 375 | 400 | 1.2477 |
| 400 | 425 | 1.2627 |
| 425 | 450 | 1.2777 |
| 450 | 475 | 1.2927 |
| 475 | 500 | 1.3077 |
| 500 | 525 | 1.3227 |
| 525 | 550 | 1.3377 |
| 550 | 575 | 1.3527 |
| 575 | 600 | 1.3677 |
| 600 | 625 | 1.3827 |
| 625 | 650 | 1.3977 |
| 650 | 675 | 1.4127 |
| 675 | 700 | 1.4277 |
| 700 | 725 | 1.4427 |
| 725 | 750 | 1.4577 |
| 750 | 775 | 1.4727 |
| 775 | 800 | 1.4877 |
| 800 | 825 | 1.5027 |
| 825 | 850 | 1.5177 |
| 850 | 875 | 1.5327 |
| 875 | 900 | 1.5477 |
| 900 | 925 | 1.5627 |
| 925 | 950 | 1.5777 |
| 950 | 975 | 1.5927 |
| 975 | 1000 | 1.6077 |
| 1000 | 1050 | 1.6302 |
| 1050 | 1100 | 1.6602 |
| 1100 | 1150 | 1.6902 |
| 1150 | 1200 | 1.7202 |
| 1200 | 1250 | 1.7502 |
| 1250 | 1300 | 1.7802 |
| 1300 | 1350 | 1.8102 |
| 1350 | 1400 | 1.8402 |
| 1400 | 1450 | 1.8702 |
| 1450 | 1500 | 1.9002 |
| 1500 | 1550 | 1.9302 |
| 1550 | 1600 | 1.9602 |
| 1600 | 1650 | 1.9902 |
| 1650 | 1700 | 2.0202 |
| 1700 | 1750 | 2.0502 |
| 1750 | 1800 | 2.0802 |
| 1800 | 1850 | 2.1102 |
| 1850 | 1900 | 2.1402 |
| 1900 | 1950 | 2.1702 |
| 1950 | 2000 | 2.2002 |
| 2000 |  | 2.2152 |

The method for establishing a smooth geometric model based on the data of the medical image of the embodiments of the disclosure could greatly improve the stepped contour of the voxel phantom, making it be more like the contour of the human organ surface and improving the reliability of the dose calculation to improve the quality of treatment.

It should be understood that the present invention could also be applied to other fields of radiation therapy which may be simulated by MCNP, such as proton, heavy ion, X-ray or gamma ray treatment, which are well known to those skilled in the art, and may also be applied to other diseases which could be treated by radiation irradiation, such as Alzheimer's disease and rheumatoid arthritis, and the tumor cells are other diseased tissues.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A method for establishing a smooth geometric model based on data of a medical image, comprising:
inputting or reading the data of the medical image;
establishing a three-dimensional medical image voxel model based on the data of the medical image;
smoothing the three-dimensional medical image voxel model by defining or reading a region of interest (ROI) boundary and smoothing the ROI boundary, wherein the ROI boundary is smoothed by:
describing the ROI boundary as a partial differential equation; and
solving the partial differential equation to obtain a solution and correcting the ROI boundary according to the solution to obtain a corrected ROI boundary; and establishing a three-dimensional voxel phantom tissue
    model based on the smoothed three-dimensional medical image voxel model, wherein the three-dimensional voxel phantom tissue model is established by:
  determining whether each of a plurality of medical image voxels in the data of the medical image is within the corrected ROI boundary;
  when one of the medical image voxels is determined to be within the corrected ROI boundary, performing manually defining a type and a density of a tissue by assigning a particular tissue and density to the one of the medical image voxels within the corrected ROI boundary, or performing:
    automatically defining a type of a ROI tissue according to a conversion relationship between the data of the medical image and tissue types,
    determining a quantity of tissue clusters of the ROI tissue, wherein the quantity of the tissue clusters of the ROI tissue is a quantity of the tissue clusters manually defined by a user plus a quantity of four tissue clusters or fourteen tissue clusters already existing in a database, and
    automatically defining a density of the ROI tissue by a conversion relationship between the data of the medical image and density values;
  when one of the medical image voxels is determined not to be within the corrected ROI boundary, performing:
    automatically defining the type of the tissue according to the conversion relationship between the data of the medical image and the tissue types,
    determining the quantity of the tissue clusters of the tissue, wherein the quantity of the tissue clusters of the ROI tissue is a quantity of the tissue clusters manually defined by a user plus a quantity of four tissue clusters or fourteen tissue clusters already existing in the database, and
    automatically defining the density of the tissue by the conversion relationship between the data of the medical image and the density values;
  establishing a three-dimensional (3D) encoding matrix with information about the tissue and the density; and
  assigning a Boron-10 concentration and establishing the 3D encoding matrix with information of the Boron-10 concentration.

2. The method according to claim 1, wherein the ROI boundary is smoothed by a finite element analysis software.

3. The method according to claim 1, wherein the ROI boundary is pre-defined or newly added in the data of the medical image, and the newly added ROI boundary is obtained by automatic judgment or manual selection, wherein the ROI boundary comprises multiple sub-geometric domains being described by partial differential equations.

4. The method according to claim 1, wherein and the three-dimensional voxel phantom tissue model is established by further establishing a 3D tissue encoding matrix and establishing a 3D density encoding matrix.

5. The method according to claim 1, being applied to a neutron capture therapy, wherein the smooth geometric model comprises a lattice card, a cell card, a surface card and a material card required for a MCNP (Monte Carlo Program) software input file.

6. A method for establishing a smooth geometric model based on data of a medical image, comprising:
  inputting or reading the data of the medical image;
  establishing a three-dimensional voxel phantom tissue model based on the data of the medical image, wherein the three-dimensional voxel phantom tissue model carries information about type and density of a tissue is established by:
    defining or reading a region of interest (ROI) boundary;
    determining whether each of a plurality of medical image voxels in the data of the medical image is within the ROI boundary;
    when one of the medical image voxels is determined to be within the ROI boundary, performing manually defining a type and a density of a tissue by assigning a particular tissue and density to the one of the medical image voxels within the ROI boundary or performing:
      automatically defining a type of a ROI tissue according to a conversion relationship between the data of the medical image and tissue types,
      determining a quantity of tissue clusters of the ROI tissue, wherein the quantity of the tissue clusters of the ROI tissue is a quantity of the tissue clusters manually defined by a user plus a quantity of four tissue clusters or fourteen tissue clusters already existing in a database, and
      automatically defining a density of the ROI tissue by a conversion relationship between the data of the medical image and density values;
    when one of the medical image voxels is determined not to be within the ROI boundary, performing:
      automatically defining the type of the tissue according to the conversion relationship between the data of the medical image and the tissue types,
      determining the quantity of the tissue clusters of the tissue, wherein the quantity of the tissue clusters of the ROI tissue is a quantity of the tissue clusters manually defined by a user plus a quantity of four tissue clusters or fourteen tissue clusters already existing in the database, and
      automatically defining the density of the tissue by the conversion relationship between the data of the medical image and the density values;
    establishing a three-dimensional (3D) encoding matrix with information about the tissue and the density; and
    assigning a Boron-10 concentration and establishing the 3D encoding matrix with information of the Boron-10 concentration; and
  smoothing the three-dimensional voxel phantom tissue model by reading the ROI boundary and smoothing the ROI boundary, wherein the ROI boundary is smoothed by:
    describing the ROI boundary as a partial differential equation; and
    solving the partial differential equation to obtain a solution and correcting the ROI boundary according to the solution.

7. The method according to claim 6, wherein the ROI boundary is smoothed by a finite element analysis software.

8. The method according to claim 6, wherein the ROI boundary is pre-defined or newly added in the data of the medical image, and the newly added ROI boundary is obtained by automatic judgment or manual selection, wherein the ROI boundary comprises multiple sub-geometric domains being described by partial differential equations.

9. The method according to claim 6, wherein the three-dimensional voxel phantom tissue model is established by:

defining a type of a tissue according to a conversion relationship between the data of the medical image and tissue types;

determining a quantity of tissue clusters of the tissue;

defining a density of the tissue by a conversion relationship between the data of the medical image and density values; and establishing a three-dimensional (3D) encoding matrix with information about the tissue and the density.

10. The method according to claim 9, wherein the three-dimensional voxel phantom tissue model is established by further assigning a Boron-10 concentration and establishing the 3D encoding matrix with information of the Boron-10 concentration.

11. The method according to claim 9, wherein the quantity of the tissue clusters is a quantity of the tissue clusters manually defined by a user, plus a quantity of four tissue clusters or fourteen tissue clusters already existing in the database, and the three-dimensional voxel phantom tissue model is established by further establishing a 3D tissue encoding matrix and establishing a 3D density encoding matrix.

12. The method according to claim 6, wherein the 3D encoding matrix with the information about the tissue and the density is established by establishing a 3D tissue encoding matrix and establishing a 3D density encoding matrix.

13. The method according to claim 6, being applied to a neutron capture therapy, wherein the smooth geometric model comprises a lattice card, a cell card, a surface card and a material card required for a MCNP (Monte Carlo Program) software input file.

* * * * *